United States Patent
Mody et al.

(10) Patent No.: US 10,711,096 B2
(45) Date of Patent: Jul. 14, 2020

(54) AQUEOUS MONOMER COMPOSITIONS AND METHODS OF MAKING AND USING THE SAME

(71) Applicant: Elevance Renewable Sciences, Inc., Woodridge, IL (US)

(72) Inventors: Kamlesh Mody, Chicago, IL (US); Daniel Mubima, Plainfield, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 16/114,443

(22) Filed: Aug. 28, 2018

(65) Prior Publication Data

US 2019/0135976 A1    May 9, 2019

Related U.S. Application Data

(63) Continuation of application No. 14/721,418, filed on May 26, 2015, now abandoned.

(60) Provisional application No. 62/004,087, filed on May 28, 2014.

(51) Int. Cl.
| | |
|---|---|
| *C08G 63/81* | (2006.01) |
| *A61Q 19/00* | (2006.01) |
| *A61K 8/37* | (2006.01) |
| *C08G 69/26* | (2006.01) |
| *C09D 177/06* | (2006.01) |
| *C08G 63/16* | (2006.01) |

(52) U.S. Cl.
CPC .............. *C08G 63/81* (2013.01); *A61K 8/37* (2013.01); *A61Q 19/00* (2013.01); *C08G 63/16* (2013.01); *C08G 69/26* (2013.01); *C09D 177/06* (2013.01); *A61K 2800/10* (2013.01)

(58) Field of Classification Search
CPC ........ C08G 63/81; C08G 69/26; C08G 63/16; A61K 8/37; A61K 2800/10; A61Q 19/00; C09D 177/06
See application file for complete search history.

(56) References Cited

U.S. PATENT DOCUMENTS

| | | | |
|---|---|---|---|
| 6,624,128 | B1 | 9/2003 | Smiley |
| 2008/0194772 | A1 | 8/2008 | Kong et al. |
| 2008/0275182 | A1 | 11/2008 | Kong et al. |
| 2011/0086206 | A1* | 4/2011 | Scheffer ............ C09D 7/63 428/195.1 |

U.S. PATENT DOCUMENTS

2015/0344620 A1    12/2015    Mody et al.

FOREIGN PATENT DOCUMENTS

| | | | | |
|---|---|---|---|---|
| EP | 0863935 | | 11/1996 | |
| EP | 2395036 | | 12/2011 | |
| GB | 950004 | A * | 2/1964 | .......... D06M 13/224 |

OTHER PUBLICATIONS

Int'l Search Report & Written Opinion of Int'l Searching Authority for PCT App. No. PCT/US2015/032389, dated Sep. 8, 2015.

* cited by examiner

*Primary Examiner* — Andrew J. Oyer
(74) *Attorney, Agent, or Firm* — Kilpatrick Townsend & Stockton LLP

(57) ABSTRACT

Aqueous compositions of carboxylic acids, carboxylate esters, and carboxylate salts are generally disclosed, including methods of using such compounds to make various polymers, including, but not limited to, polyesters, polyamides, and polycarbamates. In certain embodiments, the carboxylic acids, carboxylate esters, and carboxylate salts are derived from a renewable source, such as a natural oil.

21 Claims, 1 Drawing Sheet

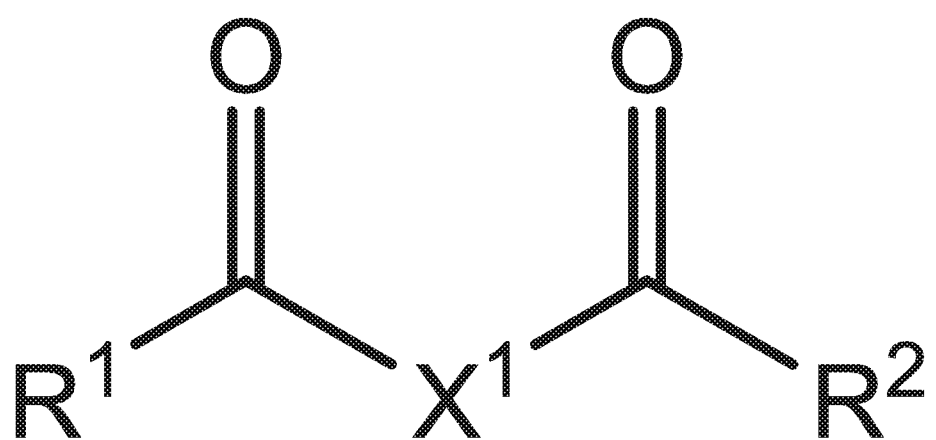

US 10,711,096 B2

AQUEOUS MONOMER COMPOSITIONS AND METHODS OF MAKING AND USING THE SAME

CROSS-REFERENCE TO RELATED APPLICATIONS

The present application is a continuation of U.S. patent application Ser. No. 14/721,418, filed May 26, 2015, which claims the benefit of priority of U.S. Provisional Application No. 62/004,087, filed May 28, 2014, both of which are hereby incorporated by reference as though fully set forth herein in their entireties.

TECHNICAL FIELD

Aqueous compositions of carboxylic acids, carboxylate esters, and carboxylate salts are generally disclosed, including methods of using such compounds to make various polymers, including, but not limited to, polyesters, polyamides, and polycarbamates. In certain embodiments, the carboxylic acids, carboxylate esters, and carboxylate salts are derived from a renewable source, such as a natural oil.

BACKGROUND

Long-chain dibasic acids, or derivatives thereof, can be used for making a wide variety of novel polymers that have improved properties relative to incumbent polymers made with short-chain dibasic acids. Such polymers can have a variety of desirable properties, such as increased toughness, increased solvent resistance, increased resistance to hydrolysis, and the like. But because long-chain dibasic acids can be especially hydrophobic, it can be difficult to use them in applications where the polymerization may occur in an aqueous environment.

Therefore, there is a continuing need to develop compounds, compositions, and methods of employing long-chain dibasic acids, or their derivatives, to carry out polymerization reactions in aqueous environments.

SUMMARY

In a first aspect, the disclosure provides aqueous compositions, the compositions including: water; and a compound of formula (I)

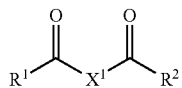

(I)

wherein:

$X^1$ is $C_{12-36}$ alkylene, $C_{12-24}$ alkenylene, $C_{12-36}$ heteroalkylene, or $C_{12-24}$ hetero-alkenylene, each of which is optionally substituted one or more times by substituents selected independently from $R^3$;

$R^1$ and $R^2$ are independently —OH, —O—$R^4$, or —O$^-$ $Z^+$, $R^3$ is a halogen atom, —OH, —NH$_2$, oxo, $C_{1-6}$ heteroalkyl, or $C_{2-6}$ heteroalkenyl;

$R^4$ is $C_{1-6}$ alkyl or $C_{2-24}$ heteroalkyl, each of which is optionally substituted one or more times by -OH; and $Z^+$ is a positively charged counterion;

provided that at least one of $R^1$ and $R^2$ is not —OH.

In a second aspect, the disclosure provides methods of forming a polymer, the methods including: providing a composition of any embodiment of the first aspect; and reacting one or more compounds of formula (I) with one or more monomers to form a polymer.

Further aspects and embodiments are provided in the foregoing drawings, detailed description and claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

The FIGURE shows a non-limiting example of a compound of certain embodiments disclosed herein, wherein: $X^1$ is $C_{12-36}$ alkylene, $C_{12-24}$ alkenylene, $C_{12-36}$ heteroalkylene, or $C_{12-24}$ hetero-alkenylene, each of which is optionally substituted one or more times; $R^1$ and $R^2$ are independently —OH, —O—$R^4$, or —O$^-$ $Z^+$, $R^4$ is $C_{1-6}$ alkyl or $C_{2-24}$ heteroalkyl, each of which is optionally substituted one or more times by —OH; and $Z^+$ is a positively charged counterion; provided that at least one of $R^1$ and $R^2$ is not —OH.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin" or an "alpha-olefin," while an olefin having a non-terminal carbon-carbon double bond can be referred to as an "internal olefin." In some embodiments, the alpha-olefin is a terminal alkene, which is an alkene (as defined below) having a terminal carbon-carbon double bond. Additional carbon-carbon double bonds can be present.

The number of carbon atoms in any group or compound can be represented by the terms: "$C_z$", which refers to a group of compound having z carbon atoms; and "$C_{x-y}$", which refers to a group or compound containing from x to y, inclusive, carbon atoms. For example, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. As a further example, a "$C_{4-10}$ alkene" refers to an alkene molecule having from 4 to 10 carbon atoms, and, for example, includes, but is not limited to, 1-butene, 2-butene, isobutene, 1-pentene, 1-hexene, 3-hexene, 1-heptene, 3-heptene, 1-octene, 4-octene, 1-nonene, 4-nonene, and 1-decene.

As used herein, the term "low-molecular-weight olefin" may refer to any one or combination of unsaturated straight, branched, or cyclic hydrocarbons in the $C_{2-14}$ range. Low-molecular-weight olefins include alpha-olefins, wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexane. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. Olefins in the $C_{4-10}$ range can also be referred to as "short-chain olefins," which can be either branched or unbranched. In one embodiments, it may be preferable to use a mixture of linear and branched $C_4$ olefins (i.e., combinations of: 1-butene, 2-butene, and/or isobutene). In other embodiments, a higher range of $C_{11-14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin ester" or "olefinic ester compounds." Further, a "terminal olefinic ester compound" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group, respectively. Non-limiting examples include "oxyalkyl" or "oxyalkylene" groups, which include groups such as: —O-(alkyl), -[-(alkylene)-O-]$_x$-alkyl, -[-(alkylene)-O-]$_x$-alkylene-, —O-[-(alkylene)-O-]$_x$-alkyl, —O-[-(alkylene)-O-]$_x$alkylene-, and the like, where x is 1 or more, such as 1, 2, 3, 4, 5, 6, 7, or 8.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the saturated carbon atoms in the alkenyl or alkenylene group can be replaced by a heteroatom (e.g., selected from nitrogen, oxygen, or sulfur, including N-oxides, sulfur oxides, and sulfur dioxides, where feasible), and is referred to as a "heteroalkenyl" or "heteroalkenylene" group, respectively. Non-limiting examples include "oxyalkenyl" or "oxyalkenylene" groups, which include groups of the following formulas: —O-(alkenyl), —[—(R$^f$)—O—]$_x$—R$^g$, —[—(R$^f$)—O—]$_x$—R$^h$—, and the like, where x is 1 or more, such as 1, 2, 3, 4, 5, 6, 7, or 8, and R$^f$, R$^g$, and R$^h$ are independently alkyl/alkylene or alkenyl/alkenylene groups, provided that each such "oxyalkenyl" or "oxyalkenylene" group contains at least one carbon-carbon double bond.

As used herein, "halogen" refers to fluorine, chlorine, bromine, or iodine. In some embodiments, "halogen" can refer to fluorine or chlorine.

As used herein, the term "oxo" refers to a =O moiety. Thus, a non-limiting example of an oxo-substituted alkyl group is a group such as —CH$_2$—(C=O)—CH$_3$. A non-limiting example of an oxo-substituted heteroalkyl group is a group such as —CH$_2$—C(=O)—O—CH$_3$.

As used herein, the term "Lewis base" refers to any compound capable of donating a pair of electrons to form a Lewis acid. The term is intended to include Bronsted bases, which are compounds capable of accepting a proton to form a Bronsted acid. Ammonia is a non-limiting example of a Lewis base, whose conjugate acid is the NH$_4^+$ cation. In some embodiments, the Lewis base is a Bronsted base.

As used herein, "polymer" refers to a substance having a chemical structure that includes the multiple repetition of constitutional units formed from substances of comparatively low relative molecular mass relative to the molecular mass of the polymer. The term "polymer" includes soluble and/or fusible molecules having chains of repeat units, and also includes insoluble and infusible networks. The term "polymer" includes compounds often referred to as oligomers.

As used herein, "monomer" refers to a substance that can undergo a polymerization reaction to contribute constitutional units to the chemical structure of a polymer.

As used herein, "polyester" refers to a polymer comprising two or more ester linkages. Other types of linkages can be included, however. In some embodiments, at least 80%, or at least 90%, or at least 95% of the linkages in the polyester are ester linkages. The term can refer to an entire polymer molecule, or can also refer to a particular polymer sequence, such as a block within a block copolymer.

As used herein, "polyamide" refers to a polymer comprising two or more amide linkages. Other types of linkages can be included, however. In some embodiments, at least 80%, or at least 90%, or at least 95% of the linkages in the polyamide are amide linkages. The term can refer to an entire polymer molecule, or can also refer to a particular polymer sequence, such as a block within a block copolymer.

As used herein, "polycarbamate" refers to a polymer comprising two or more carbamate (urethane) linkages. Other types of linkages can be included, however. In some embodiments, at least 80%, or at least 90%, or at least 95% of the linkages in the polycarbamate are carbamate linkages. The term can refer to an entire polymer molecule, or can also refer to a particular polymer sequence, such as a block within a block copolymer.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Aqueous Monomer Compositions

In a certain aspects, the disclosure provides aqueous compositions, the compositions including: water; and a compound of formula (I)

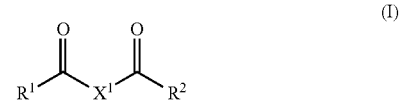

wherein:
$X^1$ is $C_{12-36}$ alkylene, $C_{12-24}$ alkenylene, $C_{12-36}$ heteroalkylene, or $C_{12-24}$ hetero-alkenylene, each of which is optionally substituted one or more times by substituents selected independently from $R^3$;
$R^1$ and $R^2$ are independently —OH, —O—$R^4$, or —O$^-$Z$^+$;
$R^3$ is a halogen atom, —OH, —NH$_2$, oxo, $C_{1-6}$ heteroalkyl, or $C_{2-6}$ heteroalkenyl;
$R^4$ is $C_{1-6}$ alkyl or $C_{2-24}$ heteroalkyl, each of which is optionally substituted one or more times by —OH; and
Z$^+$ is a positively charged counterion;
provided that at least one of $R^1$ and $R^2$ is not —OH.

Any embodiments of the compound of formula (I) can be employed. For example in some embodiments, $X^1$ is $C_{12-36}$ alkylene or $C_{12-36}$ heteroalkylene, each of which is optionally substituted one or more times by substituents selected independently from $R^3$. In some further embodiments, $X^1$ is $C_{12-36}$ alkylene, which is optionally substituted one or more times by substituents selected independently from $R^3$. In some further embodiments, $X^1$ is $C_{12-36}$ alkylene, which is optionally substituted one or more times with substituents selected independently from –OH and $C_{1-6}$ oxyalkyl, e.g., —O($C_{1-6}$ alkyl). In some further embodiments, $X^1$ is $C_{12-20}$ alkylene, optionally substituted one or more times with substituents selected independently from —OH and $C_{1-6}$ oxyalkyl, e.g., —O($C_{1-6}$ alkyl). In some such embodiments, $X^1$ is —(CH$_2$)$_{12}$—, —(CH$_2$)$_{14}$—, —(CH$_2$)$_{16}$—, —(CH$_2$)$_{18}$—, —(CH$_2$)$_{20}$—, or —(CH$_2$)$_{22}$—. In some further such embodiments, $X^1$ is —(CH$_2$)$_{16}$—.

In some other embodiments, $X^1$ is $C_{12-36}$ heteroalkylene, which is optionally substituted one or more times by substituents selected independently from $R^3$. In some such embodiments, $X^1$ is $C_{12-36}$ oxyalkylene, which is optionally substituted one or more times by substituents selected independently from $R^3$. In some further such embodiments, $X^1$ is $C_{12-36}$ oxyalkylene, which is optionally substituted one or more times with substituents selected independent from oxo, —OH, and $C_{1-6}$ oxyalkyl. In some further such embodiments, $X^1$ is a moiety of formula (II)

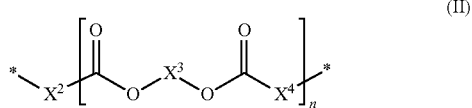

(II)

wherein: $X^2$ and $X^4$ are independently $C_{12-20}$ alkylene; $X^3$ is $C_{2-10}$ alkylene; and n is an integer from 1 to 10. In some such embodiments, $X^2$ and $X^4$ are independently —(CH$_2$)$_{12}$—, —(CH$_2$)$_{14}$—, —(CH$_2$)$_{16}$—, —(CH$_2$)$_{18}$—, —(CH$_2$)$_{20}$—, or —(CH$_2$)$_{22}$—. In some further such embodiments, $X^2$ and $X^4$ are —(CH$_2$)$_{16}$—. In some further such embodiments, $X^3$ is —(CH$_2$)$_2$—, —(CH$_2$)$_4$—, —(CH$_2$)$_6$—, —(CH$_2$)$_8$—, or —(CH$_2$)$_{10}$—. In some further such embodiments, $X^3$ is —(CH$_2$)$_2$—, —(CH$_2$)$_4$—, or —(CH$_2$)$_6$—. In some further such embodiments, $X^3$ is —(CH$_2$)$_6$—. In some further such embodiments, n is 1, 2, 3, 4, or 5. In some further such embodiments, n is 1, 2, or 3. In some even further such embodiments, n is 2.

In some further embodiments of any of the above embodiments, $R^1$ is —OH. In some further embodiments of any of the above embodiments, $R^1$ is —O$^-$ $Z^+$. In some further embodiments of any of the above embodiments, $R^1$ is —O—$R^4$.

In some further embodiments of any of the above embodiments, $R^2$ is —OH. In some further embodiments of any of the above embodiments, $R^2$ is —O$^-$ $Z^+$. In some further embodiments of any of the above embodiments, $R^2$ is —O—$R^4$.

In some further embodiments of any of the above embodiments, $Z^+$ is the conjugate acid of a Lewis base. In some embodiments, $Z^+$ is an ammonium compound, i.e., a quaternary ammonium cation that can be optionally substituted with 1 to 4 organic moieties. In some such embodiments, the ammonium compound is a compound of formula (III):

(III)

wherein $R^5$, $R^6$, $R^7$, and $R^8$ are independently a hydrogen atom or a $C_{1-10}$ alkyl, where the alkyl group is optionally substituted one or more times with substituents selected independently from the group consisting of a halogen atom, —OH, —NH$_2$, and $C_{1-6}$ heteroalkyl. In some further embodiments, $R^5$, $R^6$, $R^7$, and $R^8$ are independently a hydrogen atom or a $C_{1-6}$ alkyl, where the alkyl group is optionally substituted one or more times with substituents selected independently from the group consisting of a halogen atom, —OH, and —O($C_{1-6}$ alkyl). In some even further embodiments, $Z^+$ is selected from the group consisting of: an unsubstituted ammonium cation (NH$_4^+$), a triethylammonium cation, and an N,N-dimethylethanolammonium cation.

In some embodiments of any of the above embodiments, $R^4$ is $C_{2-24}$ heteroalkyl, which is optionally substituted one or more times by —OH. In some such embodiments, $R^4$ is $C_{2-24}$ oxyalkyl, which is optionally substituted one or more times by —OH. In some such embodiments, $R^4$ is —CH$_2$CH$_2$—(O—CH$_2$—CH$_2$)$_p$—O—$R^9$, wherein p is an integer from 0 to 10, and $R^9$ is a hydrogen atom, methyl, or ethyl.

The aqueous compositions disclosed herein can contain any suitable amount of water. In some embodiments, the composition comprises at least 40% by weight, or at least 50% by weight, or at least 60% by weight, or at least 70% by weight, or at least 80% by weight, or at least 90% by weight, or at least 95% by weight, or at least 97% by weight, water.

The aqueous compositions disclosed herein can contain any suitable additional ingredients, whether or not miscible and/or soluble in water. For example, in some embodiments, the composition further comprises an additional solvent, a co-solvent, a surfactant, a co-surfactant, an emulsifier, a natural or synthetic colorant, a natural or synthetic fragrance, an antioxidant, a corrosion inhibitor, or an antimicrobial agent. Such solvents or co-solvents can be miscible in water (e.g., alcohols, etc.) or at least partially immiscible in water.

The compounds of formula (I) can exist in the aqueous medium in any suitable form. In some embodiments, the compounds are at least partially solubilized by the aqueous medium, meaning that the composition is a solution. In some embodiments, at least a portion of the compounds are not solubilized and exist in the medium as particles, i.e., as dispersed particles, leading to an embodiment where the composition is a dispersion.

Any other additional ingredient can be included in the composition, as long as their inclusion is not inconsistent with the utility of the composition.

Methods of Making Monomer Compounds

In the above embodiments, the aqueous composition can include at least one compound that can serve as a monomer, such as a compound of formula (I). Such compounds can be made by any suitable means. For example, in some embodiments, a long-chain dibasic acid, such as 1,18-octadecanedioic acid, can be converted to a salt by treating it with base in the presence of suitable counterions (e.g., ammonium cations). In other embodiments, a long-chain dibasic acid, such as 1,18-octadecanedioic acid, can be converted to an ester by transesterification in the presence of an alcohol.

Derivation from Renewable Sources

The compounds employed in any of the aspects or embodiments disclosed herein can, in certain embodiments, be derived from renewable sources, such as from various natural oils or their derivatives. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin (or short-chain olefin) is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some embodiments, the short-chain olefin is 1-butene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, the unsaturated esters may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, multiple metathesis reactions can also be employed. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

For example, multiple metathesis can be employed to make the dibasic acid compounds used to make the diesters disclosed herein. In some embodiments, alkyl (e.g., methyl) esters of 9-decenoic acid, 9-undecenoic acid, 9-dodecenoic acid, or any combination thereof, can be reacted in a self-metathesis reaction or a cross-metathesis to generate various unsaturated dibasic alkyl esters, such as dimethyl 9-octadecendioate. Such compounds can then be converted to dibasic acids by hydrolysis or via saponification followed by acidification. If a saturated dibasic acid is desired, the compound can be hydrogenated, either before conversion to the acid or after. Dibasic acids of other chain lengths can be made by analogous means.

The conditions for such metathesis reactions, and the reactor design, and suitable catalysts are as described below with reference to the metathesis of the olefin esters. That discussion is incorporated by reference as though fully set forth herein.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

Methods of Making Polymers

In certain aspects, the disclosure provides methods of forming a polymer, the methods including: providing a composition (e.g., an aqueous composition) of any of the above embodiments; and reacting one or more compounds of formula (I) with one or more additional monomers to form a polymer. In some embodiments, the one or more additional monomers are polyols, such as diols, and the formed polymer is a polyester. In some other embodiments, the one or more monomers are polyamines, such as diamines, and the formed polymer is a polyamide. In some other embodiments, the one or more monomers are polyisocyanates, such as diisocyanates, and the formed polymer is a polycarbamate.

Use in Sizing Compositions

The aqueous compositions disclosed above, or the polymers formed therefrom, can be used and/or formed in any suitable application, such as part of a sizing composition for a cellulosic fiber (e.g., starch, cellulose, hydroxylated celluloses, such as hydroxyalkylcelluloses) and other hydroxyl-containing polymers. For example, in some embodiments, the composition, or polymers formed therefrom, is used as a coating or sizing for a cellulosic fiber, e.g., as a coating for paper or other wood and/or products. In some other embodiments, the composition, or a polymer formed therefrom, is used as a coating or sizing for a glass fiber.

Use in Personal Care Compositions

The aqueous compositions disclosed above, or the polymers formed therefrom, can be used in certain personal care compositions, e.g., as emulsifiers for various ingredients, such as fatty acids (e.g., stearic acid) and glycerol.

EXAMPLES

The following Examples illustrate certain aspects and embodiments of the compounds, compositions, and methods disclosed herein. The Examples merely illustrate particular embodiments and aspects of the disclosed subject matter, and are not intended to provide substantive limits on the scope of the claimed subject matter.

Example 1—Aqueous Composition of 1,18-Octadecandioate

About 60 grams of warm water (68° C.) was added to a flask fitted with a condenser, followed by the addition of 10 grams of 1,18-octadecanedioic acid (ODDA) with stirring. In a separate vial, 5.5 mL of triethylamine was mixed with an equal volume of water, and was added to the ODDA mixture. The mixture was heated to 90° C., while adding additional water, if necessary. The composition was cooled to room temperature to obtain an aqueous composition of 1,18-octadecanedioate.

Example 2—Aqueous Composition of 1,18-Octadecandioic Acid Derivative

A 150-gram sample of ODDA was added to a flask fitted with a condenser and a receiver. Then, 38 grams of 1,6-hexanediol and a small amount of tin catalyst was added. The mixture was heated to 190° C. until all of the reaction water was removed. Then, 30 grams of dimethylethanolamine (DMEA) in 90 grams of water was added to the mixture. Additional water was added until the contents of the flask were converted to a dispersion of fine particles dispersed in the aqueous medium. The dispersion was then cooled to room temperature.

What is claimed is:

1. A method of forming a polymer, the method comprising:
   (a) providing a composition comprising: water and a compound of formula (I)

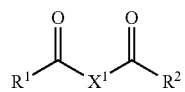

(I)

wherein:
X¹ is $C_{12-20}$ alkylene, optionally substituted one or more times with substituents selected independently from —OH and $C_{1-6}$ oxyalkyl;
R¹ and R² are independently —OH, —O—R⁴, or —O⁻Z⁺;
R⁴ is $C_{1-6}$ alkyl or $C_{2-24}$ heteroalkyl, each of which is optionally substituted one or more times by —OH; and
Z⁺ is a positively charged counterion;
provided that at least one of R¹ and R² is not —OH; and
(b) reacting one or more compounds of formula (I) with one or more monomers to form a polymer.

2. The method of claim 1, wherein the one or more monomers are polyols and the formed polymer is a polyester.

3. The method of claim 1, wherein the one or more monomers are polyamines and the formed polymer is a polyamide.

4. The method of claim 1, wherein the one or more monomers are polyisocyanates and the formed polymer is a polycarbamate.

5. The method of claim 2, wherein the polyols are diols.

6. The method of claim 3, wherein the polyamines are diamines.

7. The method of claim 4, wherein the polyisocyanates are diisocyanates.

8. The method of claim 1, wherein X¹ is —(CH₂)12-, —(CH₂)14-, —(CH₂)16-, —(CH₂)18-, —(CH₂)20-, or —(CH₂)22-.

9. The method of claim 8, wherein X¹ is —(CH₂)16-.

10. The method of claim 1, wherein R¹ is —OH.

11. The method of claim 1, wherein R¹ is —O⁻Z⁺.

12. The method of claim 1, wherein R¹ is —O—R⁴.

13. The method of claim 11, wherein R² is —O⁻Z⁺.

14. The method of claim 12, wherein R² is —O—R₄.

15. The method of claim 13, wherein Z⁺ is the conjugate acid of a Lewis base.

16. The method of claim 15, wherein Z⁺ is an ammonium compound.

17. The method of claim 16, wherein the ammonium compound is a compound of formula (III):

(III)

wherein:
R⁵, R⁶, R⁷, and R⁸ are independently a hydrogen atom or a $C_{1-10}$ alkyl, where the alkyl group is optionally substituted one or more times with substituents selected independently from the group consisting of a halogen atom, —OH, —NH₂, and $C_{1-6}$ heteroalkyl.

18. The method of claim 17, wherein R⁵, R⁶, R⁷, and R⁸ are independently a hydrogen atom or a $C_{1-6}$ alkyl, where the alkyl group is optionally substituted one or more times with substituents selected independently from the group consisting of a halogen atom, —OH, and —O($C_{1-6}$ alkyl).

19. The method of claim 18, wherein Z⁺ is selected from the group consisting of:
ammonium cation, triethylammonium cation, and N,N-dimethylethanolammonium cation.

20. The method of claim 14, wherein R⁴ is $C_{2-24}$ oxyalkyl, which is optionally substituted one or more times by —OH.

21. The method of claim 20, wherein R⁴ is —CH₂CH₂—(O—CH₂—CH₂)$_p$—O—R⁹, wherein p is an integer from 0 to 10, and R⁹ is a hydrogen atom, methyl, or ethyl.

* * * * *